Figure 1:
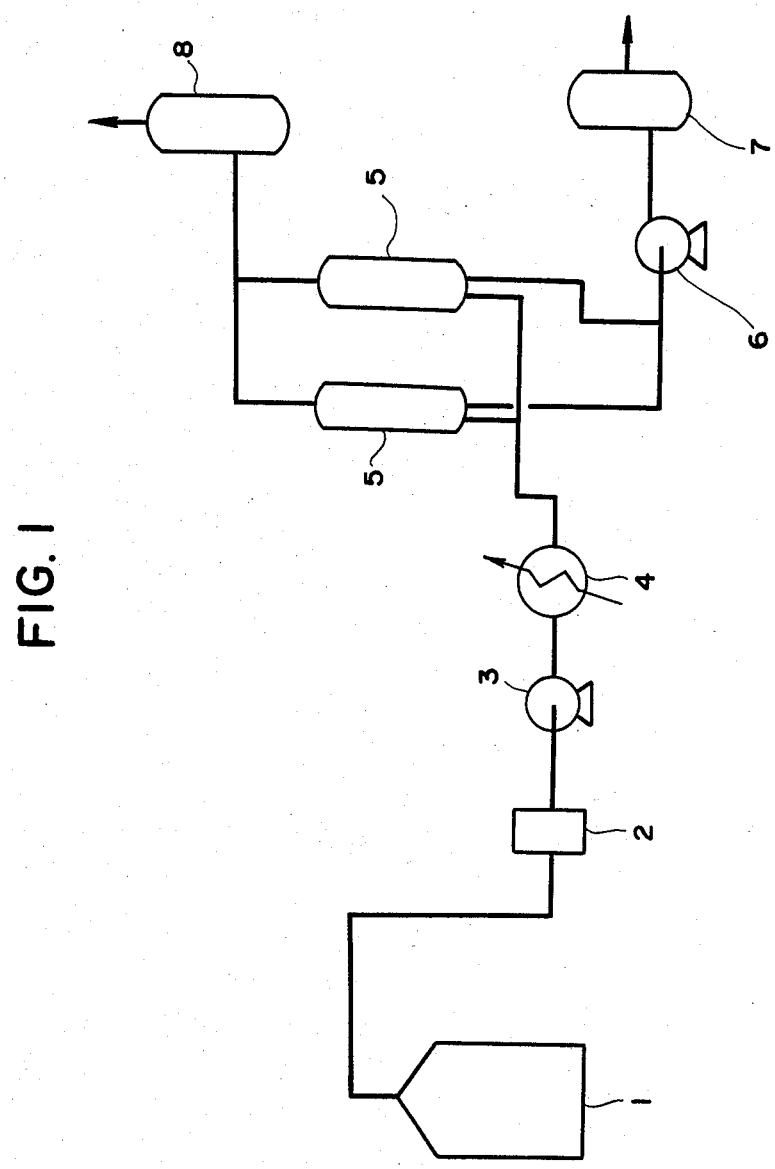

United States Patent [19]

Uno et al.

[11] Patent Number: 4,581,044
[45] Date of Patent: Apr. 8, 1986

[54] PROCESS FOR SEPARATING CARBONIC ACID GAS FROM METHANE-RICH GAS

[75] Inventors: Masaru Uno; Satoshi Ihara, both of Akashi; Takeo Tanabe, Nara; Masakatsu Hiraoka, Uji, all of Japan

[73] Assignee: Seitetsu Kagaku Co., Ltd., Hyogo, Japan

[21] Appl. No.: 581,208

[22] Filed: Feb. 21, 1984

Related U.S. Application Data

[63] Continuation of Ser. No. 368,326, Apr. 14, 1982, abandoned.

[30] Foreign Application Priority Data

Jan. 12, 1982 [JP] Japan .................................. 57-3595
Mar. 18, 1982 [JP] Japan .................................. 57-44194

[51] Int. Cl.$^4$ .......................................... B01D 53/04
[52] U.S. Cl. .......................................... 55/25; 55/75
[58] Field of Search ............... 55/25, 26, 58, 68, 73, 55/75, 76, 163, 389

[56] References Cited

U.S. PATENT DOCUMENTS

| | | | |
|---|---|---|---|
| 3,594,983 | 7/1971 | Yearout | 55/58 |
| 3,619,984 | 11/1971 | Domine et al. | 55/25 |
| 3,634,028 | 1/1972 | Hohne | 55/73 |
| 3,638,398 | 2/1972 | Domine et al. | 55/25 |
| 3,751,878 | 8/1973 | Collins | 55/58 |
| 3,801,513 | 4/1974 | Munzner et al. | 55/75 |
| 3,841,058 | 10/1974 | Templeman | 55/58 |
| 4,013,429 | 3/1977 | Sircar et al. | 55/58 |
| 4,077,779 | 3/1978 | Sircar et al. | 55/25 |
| 4,234,322 | 11/1980 | De Meyer et al. | 55/25 |
| 4,256,469 | 3/1981 | Leitgeb | 55/25 |
| 4,340,398 | 7/1982 | Doshi et al. | 55/25 |
| 4,376,640 | 3/1983 | Vo | 55/26 |

FOREIGN PATENT DOCUMENTS

| | | | |
|---|---|---|---|
| 633137 | 12/1949 | United Kingdom | 55/25 |
| 2000047 | 1/1979 | United Kingdom | 55/68 |

*Primary Examiner*—Ivars Cintins
*Attorney, Agent, or Firm*—Jordan and Hamburg

[57] ABSTRACT

A process for separating and recovering carbonic acid gas from a methane-rich gas containing the same by a pressure swing means comprising contacting the methane-rich gas with an adsorbent for carbonic acid gas at a high pressure to obtain a refined methane gas and then desorbing the carbonic acid from the carbonic acid gas-adsorbed adsorbent at a low pressure to obtain a substantially pure carbonic acid gas.

10 Claims, 2 Drawing Figures

FIG. I

PROCESS FOR SEPARATING CARBONIC ACID GAS FROM METHANE-RICH GAS

This application is a continuation of application Ser. No. 368,326, filed Apr. 14, 1982, now abandoned.

This invention relates to a process for separating and recovering acidic gases such as carbonic acid gas from a methane-rich gas by a pressure swing method, that is an alternate pressure variation method.

With the recent raise in energy cost, gases obtained by a methane fermentation method have been reconsidered as a substitute energy source.

The methane fermentation gases contain carbonic acid gas in a large proportion. For example, methane fermentation gases obtained by digestion of sewage and sludge, which gases are typical of methane fermentation gases, usually contain 35–40 vol. % of carbonic acid gas. Further, biomass gases obtained by means of methane fermentation of the biomass usually contain about 50% by volume of carbonic acid gas.

For this reason, such methane-rich gases (hereinafter referred to as "methane gas" for brevity) are low in calorific value and are limited in use. However, a methane gas will be converted to a high calorific gas by removing therefrom the carbonic acid gas contained therein and the high calorific gas so obtained is effective for use as fuel.

Natural gas is valuable as a source for clean energy and has been increasingly demanded.

However, natural gas obtained from under the ground will vary in composition depending on the site from which the gas is obtained, and it is usually composed mainly of methane. It further contains 2–10 vol. % of hydrocarbons such as ethylene, ethane and propane, 0.5–50 vol. % of carbonic acid gas and about 1–3 vol. % of hydrogen sulfide and the like, among which carbonic acid gas is an incombustible gas which undesirably lowers the natural gas in calorific value. In addition, acidic gases containing sulfur-containing compounds such as hydrogen sulfide are not desirable as fuel since they tend to corrode apparatuses in which gases containing the acidic ones are used For the aforementioned reason, it is not preferable to use natural gas as it is obtained and it is necessary to remove the acidic gases from natural gas.

Conventional methods for removing carbonic acid gas from starting gases containing the same generally include a chemical absorption method comprising absorbing carbonic acid gas with an alkali absorbing solution such as an amine aqueous solution or potassium carbonate aqueous solution and then heating the thus used solution for regeneration and a water absorption method comprising absorbing carbonic acid gas with water under a high pressure by means of differences in solubility and then reducing the high pressure to liberate the carbonic acid gas therefrom. However, the former requires a large amount of heat energy and the latter requires a high pressure of about 30 Kg/cm$^2$·G for physical absorption thereby incurring a high cost for the removal of carbonic acid gas with the attendant imperfect separation thereof. Thus, these conventional methods are not suitable as methods for industrially separating and recovering acidic gases such as carbonic acid gas from a methane gas containing the acidic gases.

Further, methods for adsorbing and separating carbonic acid gas by means of adsorption phenomena are exemplified by a thermal swing adsorption method and a purge gas stripping desorption method.

In the former method, the used adsorbent is regenerated by heating it to about 200° C. in a stream of gases to be treated, the product gases so treated or other gases, the amount of the stream flowed being 10–20% of that of the gases to be treated. Thus, this method requires a large amount of heat for said heating. Further, this conventional method is disadvantageous in that the time cycle is long since the adsorbing operation is resumed after cooling of the adsorbent subsequent to the heating thereof, the carbonic acid gas desorbed decreases in concentration since the gases to be treated are flowed for said regeneration and the adsorbent decreases in strength and is shortened in lifetime since repeated exposure thereof to alternate high and low temperatures. Accordingly, this method may be used satisfactorily only for removal of carbonic acid gas in a minute amount usually in the order of up to several thousand p.p.m. for example.

In the latter method (purge gas stripping desorption method), it is disadvantageous that since the used adsorbent is regenerated by flowing a large amount of air or nitrogen gas for desorption without heating, desorption is not sufficiently carried out, the effective adsorbability per unit of adsorbent is low and the amount of adsorbent used per unit of gases to be treated increases. It is also disadvantageous that carbonic acid gas to be desorbed is diluted with a large amount of a regenerating gas and, therefore, the carbonic acid gas so desorbed will hardly be used for any purposes.

In contrast, the pressure swing method used in this invention comprises carrying out the adsorption at a high pressure and the desorption at a low pressure. This method is advantageous over said conventional methods in that heating and a regenerating gas are unnecessary for the regeneration of used adsorbent, a less amount of adsorbent is required per unit of gases to be treated since the time cycle can be shortened, even to-be-treated gases containing carbonic acid gas in a high concentration may be treated for removal of the carbonic acid gas and the carbonic acid gas desorbed may be used for many purposes such as the production of liquefied carbonic acid since the desorbed carbonic acid gas is high in concentration.

Japanese patent application Laid-Open Gazette No. 56-118791 discloses a method comprising contacting a methane fermentation gas with water in a tank and withdrawing the gas-absorbed water from the tank to liberate the gas into the air. However, the method so disclosed can only remove the carbonic acid gas which cannot effectively be utilized. It appears unknown that carbonic acid gas was recovered from a methane fermentation gas containing the same and the gas so recovered was effectively utilized for some purposes. Further, with respect to natural gas, no methods other than said known methods have been known up to this time, either.

In view of this, the present inventors found that carbonic acid gas and the like may be removed and recovered at a low cost from a methane gas containing the same by the pressure swing method wherein adsorbent is used, thus accomplishing this invention.

The primary object of this invention is to provide a process for refining a methane gas at a low cost.

This object may be achieved by removing and recovering carbonic acid gas and other acidic gases from a methane-rich gas containing the same by the use of the pressure swing method.

According to this invention, the adsorption is carried out at a low pressure, the necessary energy is only electric power necessary for pressurizing gases to be treated and such energy is unnecessary in a case where natural gas itself has a pressure or in the case of gases from a pressurized fermenting tank, whereby the gases to be treated may be refined extremely conveniently. Furthermore, in cases where natural gas itself has no pressure, it must of course be pressurized for being sent even if it is not refined and the natural gas leaving an apparatus for carrying out the method of this invention is required to have approximately the same pressure as that at the inlet of the subsequent apparatus; therefore, it does not follow that the electric power is consumed only for the apparatus for carrying out the process of this invention. In any events, the process of this invention renders it possible to separate or remove carbonic acid gas and the like at a low cost. In addition, biomass gases containing carbonic acid gas in a high concentration and evolved at a low pressure may be treated by the pressure swing method of this invention to remove the carbonic acid gas at a comparatively low adsorbing pressure and recover the carbonic acid gas so removed. Biomass gases are obtained by methane fermentation of terrestrial vegetables, seaweeds or the like.

In the pressure swing method of this invention, the higher the adsorbing pressure is, the larger the amount of gases adsorbed per unit of adsorbent is. Thus the apparatus for carrying out the method of this invention may advantageously be made in compact size, however, it is not recommendable that the adsorbing pressure used be very high since this incurs an increase in electric power needed and in cost of a compressor used. It is of course unnecessary to take the trouble to lower the pressure of natural gas if the original pressure thereof is high. If the pressure of gases to be treated is required to be raised, then it should preferably be raised to 2-5 $Kg/cm^2 \cdot G$ from the view-point of the overall cost. If, on the other hand, the pressure is lower than the above, then the apparatus must disadvantageously be of a large size.

The adsorbents used herein include carbon molecular sieve, zeolite molecular sieve, silica gel, alumina gel and other commercially available various adsorbents, among which, as compared with the other adsorbents, carbon molecular sieve has the following advantages:

(1) The adsorbent allows the amount of carbonic acid gas adsorbed per unit of the adsorbent to be large.

(2) The adsorbent has high moisture resistance and this makes it unnecessary to preliminarily dry the adsorbent if gases to be treated contain moisture. More particularly, carbon molecular sieve is capable of adsorbing and desorbing even the moisture of the gases to be treated, while it is necessary to preliminarily dry the gases to be treated in a case where zeolite molecular sieve is used as the adsorbent (When zeolite is used, it will adsorb moisture thoroughly and the moisture so adsorbed will be difficult to desorb. Therefore, moisture will gradually be accumulated in the zeolite thereby to decrease its strength and cause its decomposition).

(3) The adsorbent having a nominal pore size of 3 Å has an excellent separating effect since it adsorbs only carbonic acid gas, not hydrocarbons at all.

(4) The adsorbent is capable of desorbing the adsorbed carbonic acid gas easily. This is because the adsorbent allows only carbonic acid gas to enter into the pores (dia. of molecule: carbonic acid gas, 2.8 Å; methane, 4.0 Å) since the pore size is about 3 Å. On the other hand, zeolite is utilized for its capability of adsorbing polar substances and, therefore, it exhibits high adsorbability thereby to make it difficult to desorb the adsorbed substances.

(5) The adsorbent, as compared with other ones, has high strength and satisfactory wear resistance and will not decrease in strength due to moisture. Thus, this adsorbent has excellent properties, a long lifetime and low chemical reactivity.

The temperature for the adsorption or desorption is not particularly limited, however, it may preferably be up to 50° C., more preferably 40-0° C.

The temperature of gases evolved in a methane fermenting tank are usually in the range of about 35° C. to about 55° C. and saturated with moisture. It is therefore desirable to cool the gases to below 40° C., preferably to about 20° C., in order to decrease the moisture. However, depending on the kind of adsorbents, it may be necessary to cool to a further low temperature in order to dehydrate and dry gases to be treated. In this respect, it is also advantageous to use carbon molecular sieve as the adsorbent as mentioned before.

This invention will be further explained by reference to FIG. 1 which is a flow sheet indicating one embodiment of this invention.

Gases evolved in a methane fermenting tank 1 usually contain impurities such as gaseous hydrogen sulfide. The gases are passed to a desulfurizer 2 and then to a compressor 3 thereby to raise the pressure of the gases to the necessary one. It is of course unnecessary to use the desulfurizer in a case where the fermentation gases do not contain hydrogen sulfide and the like; in this case, the gases to be treated are raised in pressure without being passed to the desulfurizer. The gases so raised in pressure are cooled by a cooler 4 to reduce the moisture content thereof and then introduced into an adsorbing means 5 packed with an adsorbent. The adsorbing means consists of at least two adsorbing towers. As the number of the towers increases, the recovery ratio increases and, at the same time, the cost of equipment also increases. Thus, the adsorbing means consists usually of 2-6 adsorbing towers. In the pressure swing apparatus according to this invention, the carbonic acid gas contained in the fermentation gases is adsorbed thereby to increase the gases in methane concentration and the thus obtained methane-rich gases are passed through a buffer tank 8 to the users. On the other hand, the carbonic acid gas adsorbed in the adsorbing tower 5 is reduced in pressure for desorption by the use of a vacuum pump 6.

In cases where the desorption is carried out at atmospheric pressure, the vacuum pump 6 is of course unnecessary. The carbonic acid gas so desorbed is passed through a reservoir 7 to the users. Depending on the purpose for which this carbonic acid is used, it is transported without any further treatment to the users or introduced into an apparatus for producing liquefied carbonic acid gas thereby to produce liquefied carbonic acid gas.

Natural gas generally contains sulfur-containing compounds such as hydrogen sulfide, and it is necessary to remove these sulfur-containing compounds. This removal may be achieved by installing, upstream of the adsorbing tower, a desulfurizing tower filled with activated carbon capable of easily adsorbing and desorbing the sulfur-containing compounds and then effecting pressure swing in the same cycle as in the adsorbing tower.

This invention will further be explained by reference to FIG. 2 which is a flow sheet indicating another embodiment of this invention.

Natural gas 1 is passed through a suction tank 2 to a compressor 3 by which it is raised in pressure to a desired one. It is a matter of course that the compressor is unnecessary in cases where the original pressure of natural gas is not lower than the desired pressure. The natural gas so raised in pressure is cooled by a cooler 4 to reduce moisture content of the gas and introduced into a desulfurizing tower 5 and then into an adsorbing tower 6. The pressure swing apparatus in FIG. 2 consists of at least two sets of a desulfurizing tower and adsorbing tower. As the number of adsorbing towers increases, not only the recovery ratio but also the cost of pressure swing apparatus increases. Thus, the pressure swing apparatus consists usually of 2-6 adsorbing towers in many cases. In the practice of this invention using the present pressure swing apparatus, the sulfur-containing compounds are adsorbed in the desulfurizing tower, the carbonic acid gas is adsorbed in the adsorbing tower and the natural gas which has been freed of the sulfur-containing compounds and carbonic acid gas is then passed through a product tank 7 to the users as a refined natural gas.

The sulfur-containing compounds and carbonic acid gas adsorbed respectively in the desulfurizing tower and adsorbing tower are desorbed at a reduced pressure by a vacuum pump 9. For desorption at atmospheric pressure, the vacuum pump is of course unnecessary.

In cases natural gas contains carbonic acid gas in a low concentration, some amounts of methane, ethane and other hydrocarbons are withdrawn from the desorbing step since the desorbed gases contain the hydrocarbons in an increased proportion. The initial portion of the desorbed gases is usually recycled to the suction tank 2 thereby to lessen the loss of the hydrocarbons, while the remaining portion 10 thereof is recovered as a gas 10. The amount of desorbed gas which is recycled may be from about 50% to about 70%, these percentages being set forth in Examples 3 and 2 respectively, which follow.

This invention will be better understood by the following non-limitative examples.

EXAMPLE 1

Gases evolved by anaerobic fermentation (so-called methane fermentation) of sewage and sludge derived from sewage disposal factories contain 35 vol. % of carbonic acid gas, 64% of methane, 1% of hydrogen and nitrogen including a minute amount of hydrogen sulfide.

The gases are passed to a desulfurizer where the minute amount of hydrogen sulfide is removed, raised in pressure to 2.5 Kg/cm$^2$·G by a compressor and then introduced into a pressure swing apparatus consisting of two towers packed with a commercially available carbon molecular sieve having a nominal pore size of 3 Å thereby to remove the carbonic acid gas and obtain a high calorific methane gas having 5 vol. % of carbonic acid gas.

The thus obtained methane gas has an increased calorific value of 8000 Kcal/Nm$^3$, while the original methane fermentation gases containing carbonic acid gas has a calorific value of 5500 Kcal/Nm$^3$. When the former gas is used as the fuel in a conventional gas engine, the efficiency is increased by about 25%. On the other hand, there is obtained a carbonic acid gas having a purity of 99% by effecting the desorption at a pressure reduced to 70 Torr by the use of the compressor. Such a highly pure carbonic acid gas has a purity enough for use as material for liquefied carbonic acid gas.

In this case, the electric power consumed is 0.12 KW/Nm$^3$ (fermentation gases) which is very economical as compared with that needed in conventional methods. Said electric power consumed corresponds to about one-third of the increased electric power generated by the gas engine whose efficiency has been enhanced, this being very economical from the view-point of energy balance.

EXAMPLE 2

Figure 2:
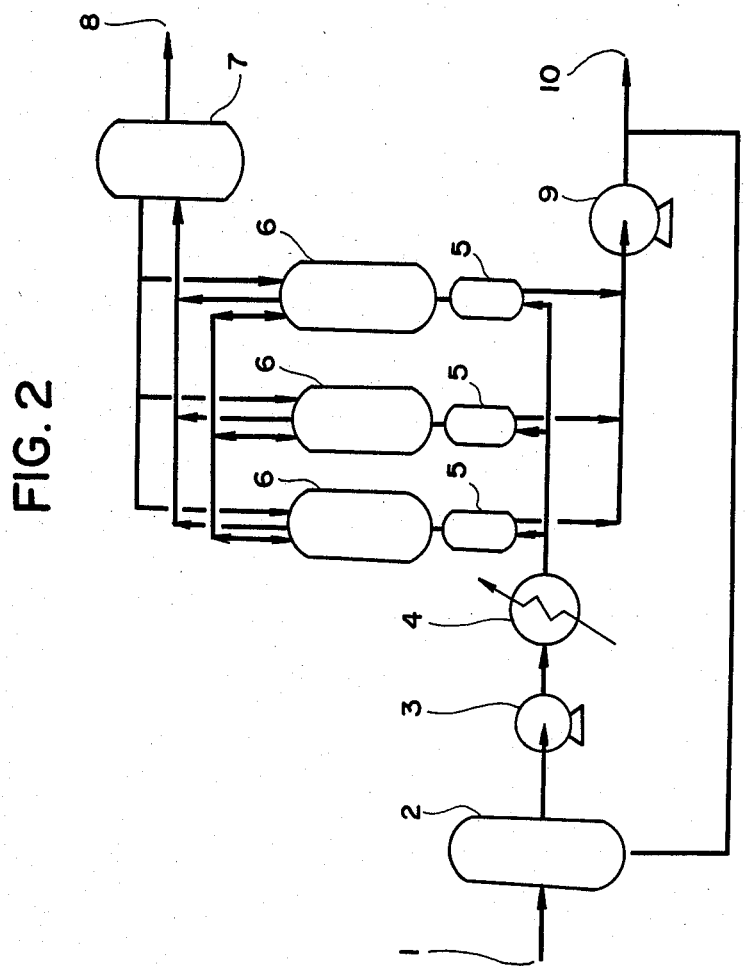

Natural gas containing 80% of methane, 4% of ethane, 15% of carbonic acid gas and 1% of hydrogen sulfide and saturated with moisture, is raised in pressure to 2.5 Kg/cm$^2$·G by a compressor and then introduced into a pressure swing apparatus consisting of 3 sets (as indicated in FIG. 2) of a desulfurizer filled with a commercially available activated carbon and an adsorbing tower filled with a commercially available carbon molecular sieve having a nominal pore size of 3 Å. In each of the adsorbing towers, the operation is performed in a 6-minutes' time cycle consisting of a 2-minutes' adsorbing step, a 1-minute's pressure equalization step, a 1-minute's reduced pressure desorbing step, a 1-minute's pressure equalization step and a 1-minute's pressure raising step as indicated in Table 1.

TABLE 1

| | 2 minutes | | 2 minutes | | 2 minutes | |
|---|---|---|---|---|---|---|
| Adsorbing tower A | Adsorption | | Pressure equalization | Desorption | Pressure equalization | Pressure raise |
| Adsorbing tower B | Pressure equalization | Desorption | Pressure equalization | Pressure raise | Adsorption | |
| Adsorbing tower C | Pressure equalization | Pressure raise | Adsorption | | Pressure equalization | Desorption |

The natural gas from the adsorbing step is freed from substantially the whole of the carbonic acid gas and contains 0.1% thereof. Further, it contains up to only 10 p.p.m. (moisture: dew point of −35° C. or below) and, thus, it is thoroughly refined.

Pressure equalization effected herein is associated with the effective utilization of energy and more particularly it is conducive to the economization of power for both the compressor and vacuum pump.

The initially desorbed gases of those desorbed at a pressure reduced to 100 Torr by the vacuum pump after the pressure equalization, contain a considerable amount (about 20% for example) of methane and are therefore recycled to the inlet of the compressor. The amount of the desorbed gases so recycled is about 70% of the whole desorbed gases during the desorbing step. The gases desorbed during the latter part of the desorbing step are discharged. The gases so discharged contain about 2% of methane and, therefore, a loss of methane is negligible for the original natural gas. The discharged gases are substantially a highly pure $CO_2$ gas (about 98% $CO_2$ content) and are fully useful as material for liquefied carbonic acid gas.

The energy needed for the operation in this case is about 0.18 $KW/Nm^3$ (the original natural gas) and is far economical as compared with other known processes for removing carbonic acid gas. In addition, the process of this invention is very advantageous in that the refining and drying of gases to be treated can be carried out at the same time.

EXAMPLE 3

Natural gas which is obtained at a self-pressure of 25 $Kg/cm^2 \cdot G$, contains 78% of methane, 2% of ethane, 20% of carbonic acid gas and no hydrogen sulfide and is saturated with moisture, is introduced into a pressure swing apparatus (as indicated in FIG. 2 except for the 3 desulfurizing towers) comprising 3 adsorbing towers filled with a commercially available carbon molecular sieve having a nominal pore size of 3 Å and then subjected to separating operation performed in a 15-minutes' time cycle consisting of a 5-minutes' adsorption step, a 5-minutes' pressure equalization and desorption step and a 5-minutes' pressure equalization and pressure raising step, in accordance with the flow sheet indicated in FIG. 2. In a case where the desorption is effected at atmospheric pressure without the use of a vacuum pump and the amount of the desorbed gas recycled is about 50% of the whole of the desorbed gas, the natural gas passing through the adsorbing tower comprises 2% of carbonic acid gas and the desorbed carbonic acid gas comprises 5% of methane gas.

It is possible to further improve the separation efficiency by effecting the desorption at superatmospheric pressure and introducing the thus desorbed gas into another pressure swing apparatus of the same kind. It is possible in this manner to reduce the concentration of methane gas in the desorbed carbonic acid gas to about 0.9%.

Accordingly, the desorbed gas from the pressure swing apparatus may further be introduced into another pressure swing apparatus of the same kind thereby to decrease not only the methane concentration in desorbed carbonic acid gas to below 1% but also the carbonic acid gas concentration in the resulting methane gas to below 1%.

EXAMPLE 4

There is provided a biomass gas containing 50% of methane, 50% of carbonic acid gas and substantially no other ingredients.

The biomass gas so provided is raised in pressure to 2.5 $Kg/cm^2 \cdot G$ and then introduced into a pressure swing apparatus consisting of two towers filled with a commercially available zeolite molecular sieve X type having a nominal pore size of 8 Å. The separating operation is performed at a desorbing pressure of 70 Torr in accordance with the flow sheet in FIG. 1 and in the same manner as in Example 1. The result is that the concentration of carbonic acid gas in the gases at the outlet of the adsorbing tower is 7% and the concentration of methane gas in the desorbed gases is 3%. These desorbed gases are composed substantially of carbonic acid gas and contain no sulfur-containing compounds. Thus, they are fully useful as material for liquefied carbonic acid gas.

What is claimed is:

1. A process for separating and recovering carbonic acid gas from a methane-rich gas containing carbonic acid gas, comprising the steps of adsorbing said carbonic acid gas from said methane-rich gas with a carbon molecular sieve having a nominal pore size of 3.0–4.0 Å as the adsorbent at a high pressure to obtain a refined methane gas, then desorbing said carbonic acid gas from the carbonic acid gas-adsorbed adsorbent at a low pressure, said methane-rich gas being maintained at a temperature up to 50° C. during said adsorption and desorption steps, and recycling an initial portion of the deadsorbed gas to the step of adsorption, thereby increasing the rate of recovery of said refined methane gas, and simultaneously enhancing the purity of the deadsorbed carbonic acid gas, so as to obtain a substantially pure carbonic acid gas.

2. A process according to claim 1, wherein the methane-rich gas is a member selected from the group consisting of a methane fermentation gas and natural gas.

3. A process according to claim 2, wherein the methane fermentation gas is a biomass gas.

4. A process according to claim 1, wherein the high pressure used in the adsorbing step is in the range of from atmospheric pressure to 50 $Kg/cm^2 \cdot G$.

5. A process according to claim 1, wherein the low pressure used in the desorbing step is in the range of 5 $Kg/cm^2 \cdot G$ down to vacuum.

6. The process of claim 1 in which the initial portion of the deadsorbed gas which is recycled is from about 50% to 70% of the whole of the desorbed gas discharged during the desorption step, said deadsorbed gas being recycled to mix with said methane-rich gas prior to said step of adsorption.

7. The process of claim 1 in which the nominal pore size of the carbon molecular sieve is about 3 Å.

8. The process of claim 1 in which the methane-rich gas is maintained at a temperature in the range of about 0° C. to 40° C. during the adsorption and desorption steps.

9. A process for separating and recovering carbonic acid gas from a supply of methane-rich gas containing carbonic acid gas, comprising the steps of conducting in a supply conductor said supply of methane-rich gas to an adsorbing means, adsorbing said carbonic acid gas from said methane-rich gas in said adsorbing means with a carbon molecular sieve having a nominal pore size within the range of 3.0 and above but less than 4 Å as the adsorbent at a high pressure to obtain a refined methane gas, then desorbing said carbonic acid gas from the carbonic acid gas-adsorbed adsorbent at a low pressure, said methane-rich gas being maintained at a temperature up to 50° C. during said adsorption and desorption steps, and recycling an initial portion of the deadsorbed gas back to said supply conductor to mix with said supply of methane-rich gas prior to said adsorption step thereby increasing the rate of recovery of said refined methane gas and simultaneously enhancing the purity of the deadsorbed carbonic acid gas so as to obtain a substantially pure carbonic acid gas.

10. A process for separating and recovering carbonic acid gas from a supply of methane-rich gas containing carbonic acid gas, comprising the steps of conducting in a supply conductor said supply of methane-rich gas to an adsorbing means, adsorbing said carbonic acid gas from said methane-rich gas in said absorbing means with a carbon molecular sieve having a nominal pore size of about 3 Å as the adsorbent at a high pressure to obtain a refined methane gas, then desorbing said carbonic acid gas from the carbonic acid gas-adsorbed adsorbent at a low pressure, said methane-rich gas being maintained at a temperature up to 50° C. during said adsorption and desorption steps, and recycling an initial portion of the deadsorbed gas back to said supply conductor to mix with said supply of methane-rich gas prior to said adsorption step, thereby increasing the rate of recovery of said refined methane gas and simultaneously enhancing the purity of the deadsorbed carbonic acid gas so as to obtain a substantially pure carbonic acid gas.

* * * * *